United States Patent
Spinelli et al.

(10) Patent No.: US 6,701,186 B2
(45) Date of Patent: Mar. 2, 2004

(54) ATRIAL PACING AND SENSING IN CARDIAC RESYNCHRONIZATION THERAPY

(75) Inventors: Julio Spinelli, Shoreview, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 217 days.

(21) Appl. No.: 09/951,699

(22) Filed: Sep. 13, 2001

(65) Prior Publication Data

US 2003/0050670 A1 Mar. 13, 2003

(51) Int. Cl.[7] .................. A61N 1/362; A61N 1/365; A61N 1/368
(52) U.S. Cl. .............................. 607/9; 607/17
(58) Field of Search .................. 607/9, 15–18, 607/25

(56) References Cited

U.S. PATENT DOCUMENTS

| | | | |
|---|---|---|---|
| 4,928,688 A | 5/1990 | Mower | 128/419 PG |
| 5,374,280 A | 12/1994 | den Dulk | 607/14 |
| 5,514,161 A | 5/1996 | Limousin | 607/9 |
| 5,584,867 A | 12/1996 | Limousin et al. | 607/9 |
| 5,902,324 A | 5/1999 | Thompson et al. | 607/9 |
| 5,954,754 A | 9/1999 | Stoop et al. | 607/28 |
| 6,070,100 A * | 5/2000 | Bakels et al. | 607/9 |
| 6,070,101 A | 5/2000 | Struble et al. | 607/9 |
| 6,081,748 A | 6/2000 | Struble et al. | 607/9 |
| 6,122,545 A | 9/2000 | Struble et al. | 607/9 |
| 6,128,532 A | 10/2000 | Stoop et al. | 607/9 |
| 6,181,968 B1 | 1/2001 | Limousin | 607/28 |
| 6,442,427 B1 * | 8/2002 | Boute et al. | 607/9 |
| 6,473,645 B1 * | 10/2002 | Levine | 607/9 |

* cited by examiner

Primary Examiner—Carl Layno
(74) Attorney, Agent, or Firm—Merchant & Gould (57) ABSTRACT

An implanted heart pacing device includes a right atrium electrode for sensing depolarization from the sino-atrial node when the device determines that the heart should proceed at a natural pulse rate and includes a left atrium electrode for providing an electrical stimulation to the left atrium when the device determines that the heart should not proceed at the natural pulse rate. One or more electrodes may also be located at one or more ventricular walls to provide electrical stimulation to the one or more ventricular walls subsequent to sensing in the right atrium or stimulating in the left atrium to resynchronize the ventricular contraction, such as for compensating for a bundle branch block. Stimulating the left atrium with a left atrium electrode when controlling the pulse rate of the heart allows the left atrium to contract early enough to avoid mitral valve closure resulting from left ventricular contraction.

39 Claims, 5 Drawing Sheets

ATRIAL PACING AND SENSING IN CARDIAC RESYNCHRONIZATION THERAPY

FIELD OF THE INVENTION

The present invention relates to cardiac resynchronization therapy in heart failure patients. More specifically, the present invention relates to using both atrial pacing and atrial sensing when applying cardiac resynchronization therapy.

BACKGROUND OF THE INVENTION

Cardiac resynchronization therapy (CRT) is a well-known method of treating heart failure patients. Oftentimes, a heart failure patient will experience a conduction disorder in a chamber of the heart caused by damage to the high-speed conduction fiber network, such as the Purkinje Fibers or Bachmann's Bundle, that is responsible for providing an electrical signal to excite a chamber, causing contraction. One form of CRT involves the use of a pacing device to provide the otherwise-faulty electrical stimulation of the chamber(s) to counteract the effects of the damaged conduction fibers. When the high-speed conduction fibers are damaged, electrical signals traveling through the heart no longer travel quickly through the high-speed fibers. The electrical signals travel much slower, because they are forced to propagate sequentially through muscle conduction, rather than high-speed fiber conduction. This results in an attenuation of the signal propagation speed and the delivery of the depolarization signal to the chamber is delayed.

This attenuation of the signal propagation speed to and through the chamber may cause the chamber to contract asynchronously relative to other chambers, or may cause one part of the chamber (e.g., the septum between the ventricles) to contract first and begin to relax before another part (e.g., the freewall of the left ventricle) contracts. This asynchronous operation can have deleterious hemodynamic effects.

CRT generally improves the pumping efficiency of the heart by providing an electrical stimulation to a later-contracting chamber, or to a later-contracting chamber portion (e.g., the left ventricle freewall) contemporaneously with the natural contraction of the earlier contracting portion, such as the septum. Because adjacent chambers and/or both walls of a ventricle contract at approximately the same time with CRT, the pumping efficiency of the heart may be significantly improved. To provide such electrical stimulation, an electrode connected to a CRT pacing device must be positioned near the delayed chamber or chamber region (e.g., the left ventricle freewall). For example, the delayed region of the left ventricle freewall may be stimulated via a branch of the coronary sinus vein that extends over the portions of the left ventricle, and a delayed region of the left atrium may be stimulated via Bachmann's bundle, the coronary sinus vein passing beneath the left atrium, or the Triangle of Koch.

When applying CRT to synchronize ventricle contraction that is otherwise asynchronous due to a bundle branch block, such as a left bundle branch block (LBBB) of the left ventricle delaying freewall contraction, the stimulation is provided synchronously with the natural conduction of the septum between the right and left ventricles. For many patients, there is no block of Bachmann's bundle between the right and left atria so no stimulation is necessary at the left atrium when the heart is beating at the natural pulse rate created by depolarization at the sino-atrial node. The right and left atria have sufficient conduction paths to the sino-atrial node and contract before the ventricles contract.

Some of these patients requiring ventricular resynchronization may also require a pacing stimulation to improve the pulse rate of the heart, such as for the bradycardia condition. Some patients requiring ventricular resynchronization may also require a rate responsive pacing device to dynamically advance the pulse rate for particular physical states of their body (e.g., during exercise) when their pulse rate does not adequately advance naturally. When controlling the pulse rate, such as for the bradycardia patient and/or for a patient requiring a rate responsive pacing device, the pulse rate is advanced through a stimulation applied by the device to the right atrium. This stimulation causes a cardiac cycle to occur sooner relative to a previous cycle than would happen naturally. These patients requiring ventricular resynchronization therapy and pulse rate control may not have an interatrial block, so that during cardiac cycles when the pulse rate is not being controlled, the conduction between the atria occurs quickly. In this case, the left atrium contracts sufficiently early so that ventricular contraction does not conflict with atrial contraction.

However, application of this stimulation by the lead also used for atrial sensing in the right atrium creates an interatrial block in most patients because the conduction from the right atrium to the left atrium will occur through muscle conduction rather than through high-speed fiber conduction. Therefore, the left atrium will contract after a delay relative to the initial stimulation. If the conduction from the right atrium proceeds quickly through the atrio-ventricular node to the septum between the ventricles, then the freewall must also be quickly paced for bundle block patients in order to maintain synchronization between the ventricular walls. However, the ventricular contraction may occur before the left atrium has completed its contraction.

Once the ventricles begin to contract, the mitral valve will be forced into a closed position. If the left atrium is contracting as the mitral valve closes in response to left ventricle contraction, then the left atrium will no longer be able to expel blood into the left ventricle and will instead pump blood back into the lungs. This condition leads to additional health problems for the patient.

If the lead used for sensing and pacing is placed in proximity to the left atrium to reduce the stimulation delay of the left atrium, then the sensing of the natural conduction will be delayed during cardiac cycles when the natural pulse rate is otherwise sufficient. This delay in sensing the natural depolarization at the left atrium location will delay the stimulation being provided to the ventricle's freewall for the bundle block patient. Ventricular contraction will remain asynchronous, and the heart's pumping efficiency will remain unimproved.

Therefore, there is a need for a cardiac resynchronization method and device that can stimulate one or more ventricular walls to synchronize ventricular contractions without creating mitral valve closure during left atrium contraction, either when allowing a natural pulse rate or when controlling the pulse rate.

SUMMARY OF THE INVENTION

Embodiments of the present invention improve cardiac resynchronization therapy by sensing a natural depolarization at the right atrium when allowing a natural pulse rate and by pacing the left atrium when controlling the pulse rate. These embodiments detect a depolarization at the sino-atrial node or other right atrium location for purposes of timing a ventricular stimulation when allowing the natural pulse rate and provide a pacing signal at the coronary sinus adjacent the left atrium or other left atrium location and a subsequent ventricular stimulation when controlling the pulse rate.

The present invention may be viewed as a method for providing resynchronization therapy to a heart. The method involves detecting whether to allow the heart to proceed at a natural pulse rate. The method also involves sensing a natural depolarization event with a first electrode in a right atrium, not stimulating a left atrium, and subsequently stimulating one or more ventricular walls with at least a second electrode during a cardiac cycle when allowing the heart to proceed at the natural pulse rate. The method additionally involves stimulating a left atrium with a third electrode and subsequently stimulating one or more ventricular walls with at least the second electrode during a cardiac cycle when not allowing the heart to proceed at the natural pulse rate.

The present invention may also be viewed as a device for providing resynchronization therapy to a heart. The device includes a processing module configured to determine whether to allow the heart to proceed at a natural pulse rate. The device also includes a first atrium electrode positioned to sense a depolarization in a right atrium, one or more ventricular electrodes positioned to provide an electrical stimulation to one or more ventricular walls, and a second atrium electrode positioned to provide an electrical stimulation to a left atrium. A sensing module in communication with the first atrium electrode is included and is configured to sense a depolarization at the first atrium electrode when the processing module determines to allow the heart to proceed at the natural pulse rate. A pacing module is included and is configured to provide electrical stimulation to the one or more ventricular electrodes subsequent to the sensing module detecting depolarization at the first atrium electrode and not stimulate the second atrium electrode when the processing module determines to allow the heart to proceed at the natural pulse rate. The pacing module is also configured to provide electrical stimulation to the second atrium electrode and subsequently provide electrical stimulation to the one or more ventricular electrodes when the processing module determines to not allow the heart to proceed at the natural pulse rate.

The present invention may also be viewed as another device for providing resynchronization therapy to a heart. The device includes a processing means configured to determine whether to allow the heart to proceed at a natural pulse rate. The device also includes a first atrium electrode means positioned to sense a depolarization in a right atrium, one or more ventricular electrode means positioned to provide an electrical stimulation to one or more ventricular walls, and a second atrium electrode means positioned to provide an electrical stimulation to a left atrium. A sensing means in communication with the first atrium electrode means is included and is configured to sense a depolarization at the first atrium electrode means when the processing means determines to allow the heart to proceed at the natural pulse rate. A pacing means is included and is configured to provide electrical stimulation to the one or more ventricular electrode means subsequent to the sensing means detecting depolarization at the first atrium electrode means and not stimulate the second atrium electrode means when the processing means determines to allow the heart to proceed at the natural pulse rate. The pacing means is also configured to provide electrical stimulation to the second atrium electrode means and subsequently provide electrical stimulation to the one or more ventricular electrode means when the processing means determines to not allow the heart to proceed at the natural pulse rate.

DETAILED DESCRIPTION

Embodiments of the present invention improve cardiac resynchronization therapy by providing both right atrium sensing and left atrium pacing functions that operate relative to whether the heart should proceed at a natural pulse rate or at a controlled pulse rate.

Figure 1:
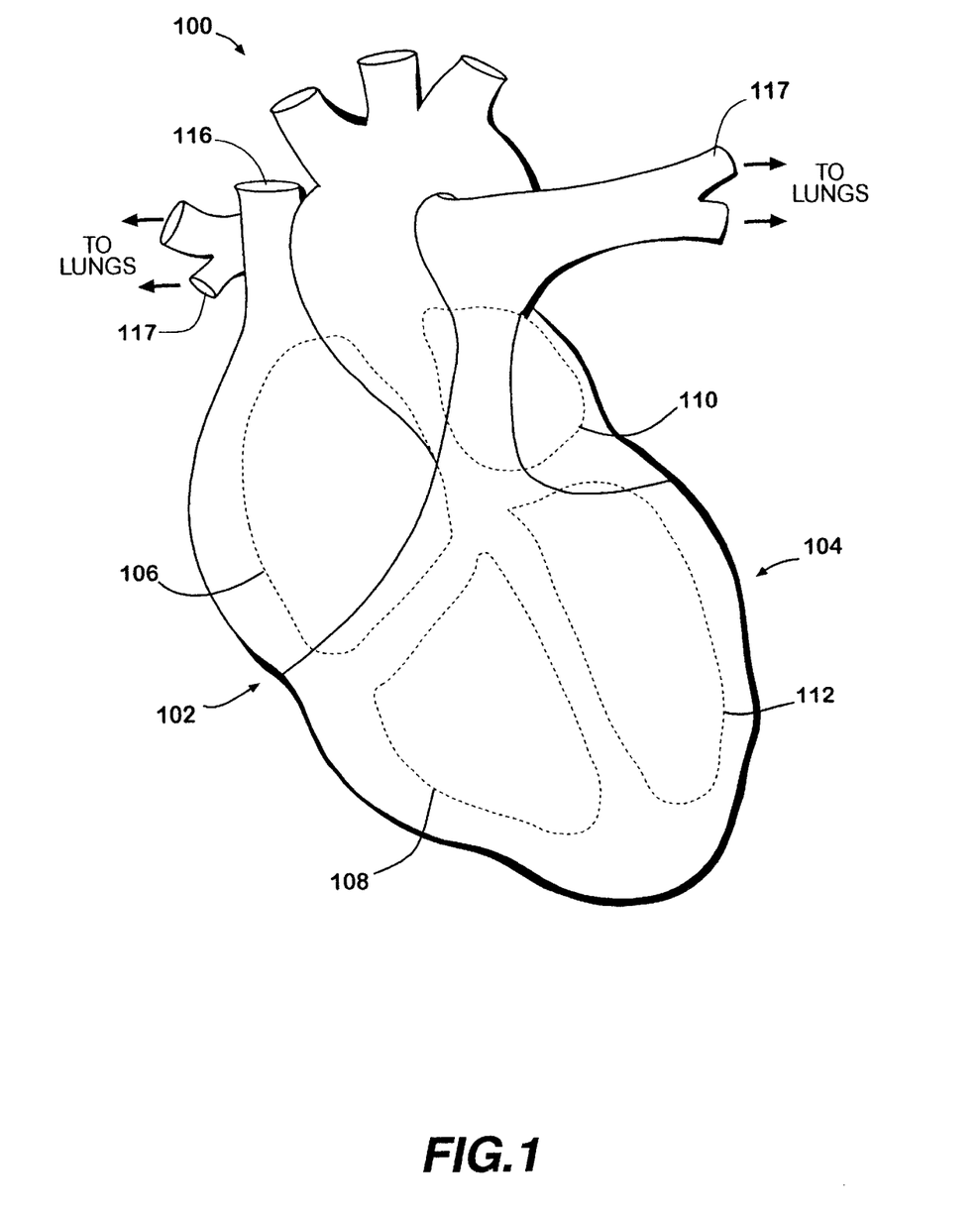
FIG. 1 is a simplified illustration depicting the primary pumping components of a human heart.

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112. Oxygen-depleted blood returning to the heart 100 from the body through the venae cavae 116 collects in the right atrium 106. When the right atrium 106 fills, the oxygen-depleted blood passes into the right ventricle 108 where it can be pumped to the lungs (not shown) via the pulmonary arteries 117. Within the lungs, waste products (e.g., carbon dioxide) are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. When the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase (e.g., systole), the ventricular muscle cells of the right and left ventricles 108, 112 contract to pump blood through the pulmonary circulation and throughout the body, respectively. Conversely, during the diastolic phase (e.g., diastole), the ventricular muscle cells of the right and left ventricles 108, 112 relax, during which the right and left atria 106, 110 contract to force blood into the right and left ventricles 108, 112, respectively.

Typically, the cardiac cycle occurs at a frequency between 60 and 100 cycles per minute and can vary depending on physical exertion and/or emotional stimuli, such as, pain or anger.

Figure 2:
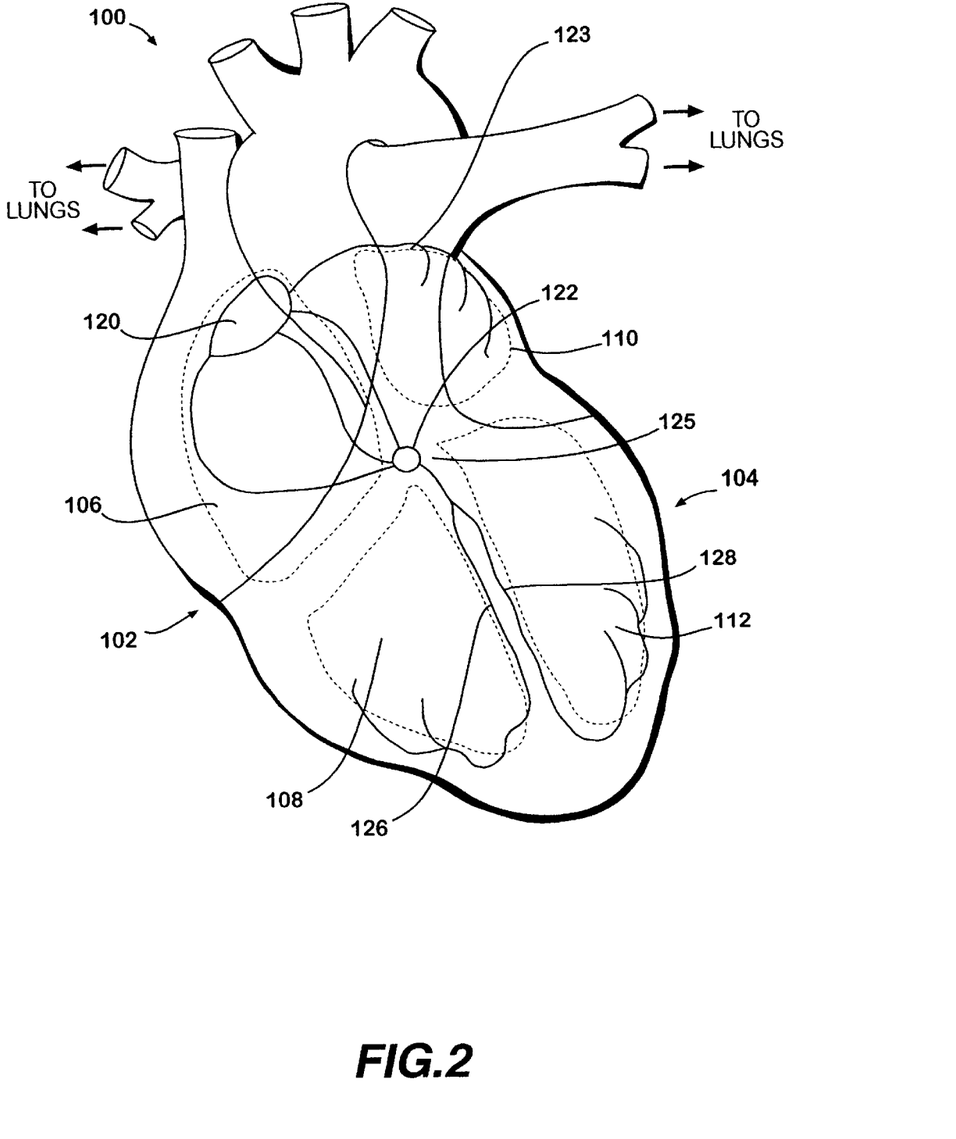
FIG. 2 is a simplified illustration depicting a human heart and the transmission paths over which a normal heart provides depolarization waves to the heart chambers.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes a sino-atrial node 120 and an atrio-ventricular node 122. The sino-atrial node 120 receives a heartbeat signal from the body's nervous system and initiates an electrical impulse (i.e., depolarization) that spreads through the muscle tissues of the right and left atria 106, 110 and the atrio-ventricular node 122. As a result, the right and left atria 106, 110 contract to pump blood into the right and left ventricles 108, 112 as discussed above. The left atrium 110 receives the electrical impulse from the sino-atrial node 120 through conduction fibers 123 known as Bachmann's Bundle. At the atrio-ventricular node 122, the electrical signal is momentarily delayed before propagating through the right and left ventricles 108, 112. The atrio-ventricular node 122 is located at an area 125 between the right and left atria 106, 110 known as the Triangle of Koch. Within the right and left ventricles 108, 112, the conduction system includes right and left bundle branches 126, 128 that extend from the atrio-ventricular node 122 via the Bundle of His 124. The electrical impulse spreads through the muscle tissues of the right and left ventricles 108, 112 via the right and left bundle branches 126, 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In a normal (i.e., healthy) heart, both the right and left atria 106, 110 contract (i.e., atrial contractions) and relax synchronously. Shortly after the atrial contractions, both the right and left ventricles 108, 112 contract (i.e., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrio-ventricular node 122, causing inadequate ventricular behavior. In cases where there exists a blockage in the high-speed conduction system responsible for causing the contraction of the ventricles (e.g., the right and/or left bundle branches 126, 128), the right and/or left ventricles 108, 112 may only be excitable through slower muscle tissue conduction. As a result, the muscular walls of the affected ventricle 108, or 112 do not contract synchronously, thereby reducing the overall effectiveness of the heart 100 to pump oxygen-rich blood throughout the body.

With CRT, when a blockage in the conduction to a freewall of a ventricle 108 or 112 exists, then an electrode is generally placed in proximity to the freewall, such as within the coronary sinus vein spanning the freewall. The pacing device delivers an electrical stimulation to the electrode and the stimulation is thereby applied to the heart 100 to induce a contraction of the freewall. The electrical stimulation to the electrode is delayed until an atrio-ventricular delay programmed into the device has expired. The atrio-ventricular delay begins once a natural depolarization is sensed in the right atrium 106 or after a stimulation is provided to the right atrium 106, depending upon whether the heart 100 is proceeding at a natural or controlled pulse rate.

Figure 3:
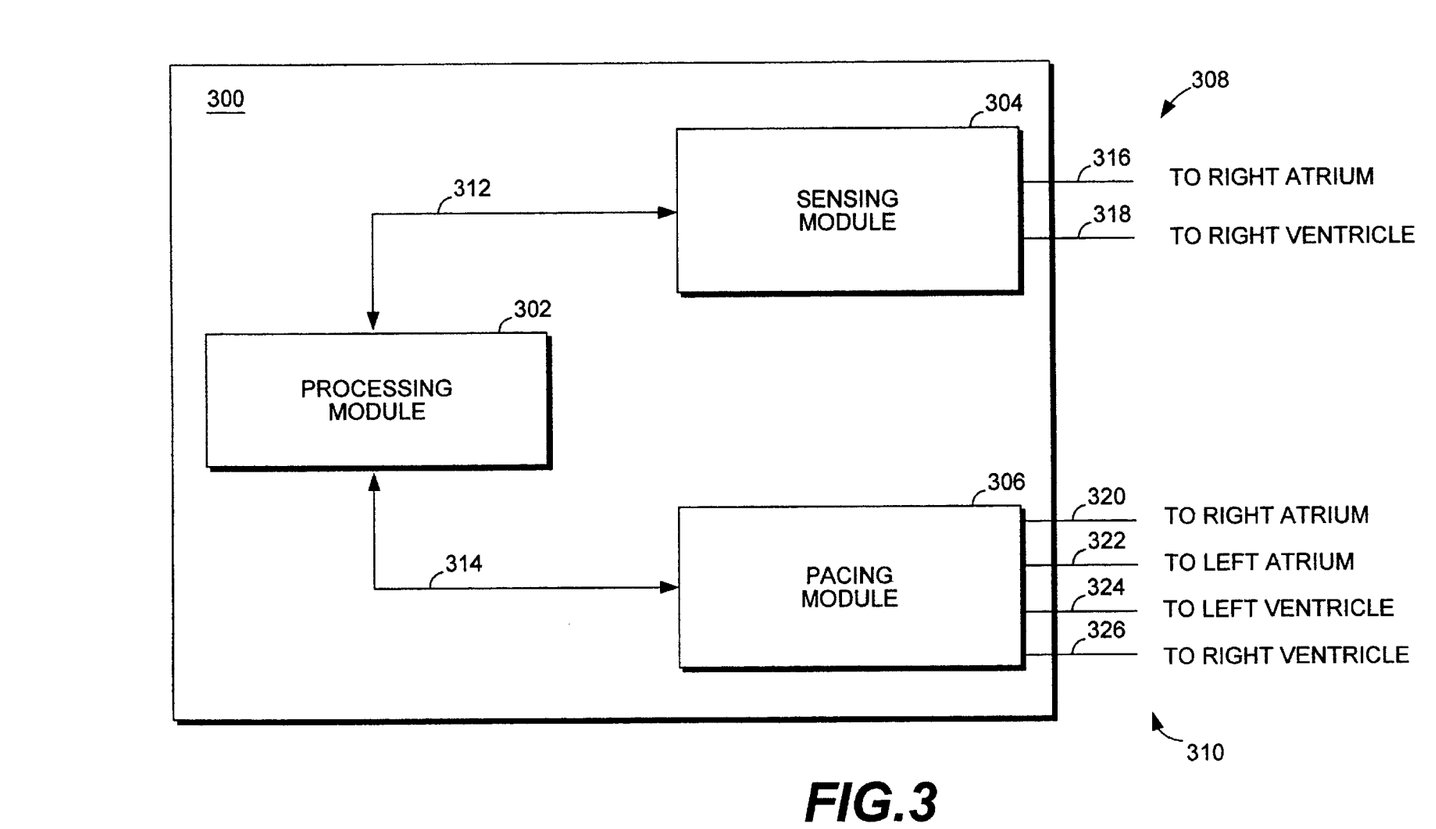
FIG. 3 is a block diagram depicting the primary components of a CRT device that is an exemplary embodiment of the present invention.

FIG. 3 is a block diagram depicting the primary components of a pacing device 300 that is an exemplary embodiment of the present invention for delivering CRT. The pacing device 300 has a processing module 302, a sensing module 304, and a pacing module 306. The processing module 302 and the sensing module 304 communicate over a sensing communication link 312. The processing module 302 and the pacing module 306 communicate with one another over a pacing communication link 314.

The pacing module 306 can deliver electrical stimulation in the form of depolarization signals to various parts of a heart 100 through pacing conductors 310. The pacing conductors 310 may include a right atrium conductor pair 320, a left atrium conductor pair 322, a left ventricle conductor pair 324, and a right ventricle conductor pair 326. As discussed below, a single conductor pair can be used to provide stimulation to both the right and left atria 108, 110 if the corresponding electrode of the single conductor pair is placed at the Triangle of Koch. Those skilled in the art will appreciate that other numbers of conductors may be used, as needed by a particular resynchronization therapy regimen. At each stimulation location, an electrode can be attached to the heart 100 to deliver the depolarization signal from the pacing module 306.

The timing of the depolarization signals delivered by the pacing module 306 over the pacing conductors 310 can be determined by the processing module 302. Each of the pacing conductors 310 can be caused to deliver a depolarization signal at a particular time in relation to the delivery of other depolarization signals. Additionally, the processing module 302 can time the delivery of depolarization signals in accordance with depolarization events detected by the sensing module 304. For example, the timing of ventricular stimulations for resynchronizing ventricular contractions can be determined in relation to stimulated or sensed atrial events. Likewise, the timing of atrial stimulations used when controlling the pulse rate of the heart 100 may be timed in relation to the conclusion of stimulated or sensed ventricular contractions or in relation to an atrial contraction of a previous cardiac cycle.

The sensing module 304 can detect electrical events that occur at particular locations on a heart 100. Electrodes that are attached to the sensing module 304 over sensing conductors 308 can detect electrical events (e.g., depolarization events) of the heart 100. The sensing conductors 308 may include a right atrium sensing conductor pair 316 and a right ventricle sensing conductor pair 318. Those skilled in the art will recognize that other numbers of sensing conductor pairs are possible as well, depending upon the particular therapies to be administered to the heart 100. As described above, the sino-atrial node 120 of the heart 100 receives a natural depolarization signal from the body's nervous system. In an exemplary embodiment of the present invention, a depolarization event occurring at the sino-atrial node 120 and sensed through the right atrium conductor 316 can be used to precisely time the delivery of a ventricular depolarization signal by the pacing module 306 through right and/or left ventricle conductor pairs 324, 326 when the heart 100 is proceeding at the natural pulse rate.

When the sensing module 304 detects a depolarization event, the sensing module 304 can notify the processing module 302 that the depolarization event has occurred. The notification may include an identification of the heart location at which the depolarization event occurred and/or the sensing conductor 308 over which the depolarization event was detected. The processing module 302 can then determine the proper pacing response to the depolarization event (if any) and can cause the pacing module 306 to respond accordingly.

In an exemplary embodiment of the present invention, the sensing module 304 can be used to monitor for a depolarization event of the sino-atrial node 120 and to notify the processing module 302 of the occurrence of the depolarization event. The processing module 302 can determine whether to allow the heart to proceed at a natural pulse rate depending upon whether the sensing module 304 detects the depolarization prior to a threshold of time being exceeded since the termination of ventricular repolarization or a previous atrial contraction. If the sensing module 306 does not detect the depolarization event of the sino-atrial node 120 prior to expiration of the time threshold, then the processing module 302 can cause the pacing module 306 to provide a depolarization signal at a right atrium location, such as at the sino-atrial node 120 through right atrium conductor pair 320, as well as at a left atrium location, such as at an electrode in the coronary sinus vein adjacent the left atrium through left atrium conductor pair 322. The pacing module 306 may alternatively deliver a depolarization signal to a left atrium location such as at an electrode at the Bachmann's Bundle 123 through conductor pair 322 instead of at the coronary sinus vein location. As another alternative, the pacing module 306 may deliver a depolarization signal to an electrode located at the Triangle of Koch 125 to stimulate both atria through a single atrium conductor pair.

After sensing an atrial depolarization when allowing the natural pulse rate, or after providing atrial pacing when controlling the pulse rate of the heart 100, the pacing module 306 can then provide electrical stimulation to one or more ventricular walls to resynchronize ventricular contraction. Prior to providing the ventricular stimulation through right ventricle pacing conductor pair 326, the sensing module 304 may monitor the right ventricle electrode through sensing conductor pair 318 to determine whether a ventricular depolarization occurs within a certain amount of time after the atrial depolarization due to conduction from the atrio-ventricular node. If not, then the pacing module 306 may apply an electrical stimulation to the right ventricle electrode through pacing conductor pair 326. The pacing module 306 also provides a electrical stimulation to the left ventricle electrode at the freewall through the left ventricle pacing conductor pair 324 to resynchronize the ventricular contraction.

Figure 4:
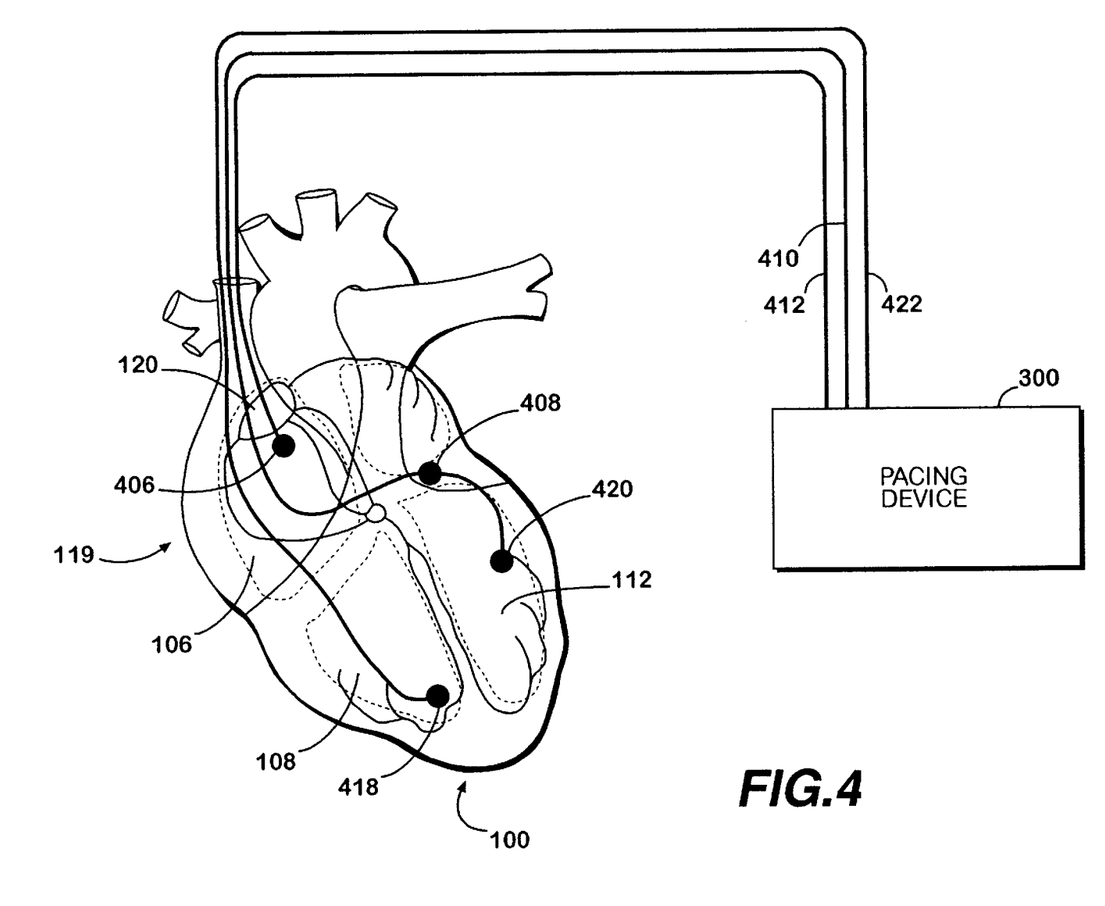
FIG. 4 is a simplified illustration depicting a human heart and the preferred locations for placement of electrodes in accordance with an exemplary embodiment of the present invention.

FIG. 4 depicts a simplified human heart 100 and the locations for placement of electrical leads and electrodes in accordance with an exemplary embodiment of the present invention. The heart 100 depicted in FIG. 4 is connected to a lead 410 that may contain both the left atrium pacing conductor 322 and the left ventricle pacing conductor 324 of the pacing device 300. The left atrium pacing conductor pair 322 leads to the left atrium electrode 408. As shown, the left atrium electrode 408 is positioned in the coronary sinus vein adjacent the left atrium 110. As discussed above, alternative locations for the left atrium electrode 408 include the Bachmann's Bundle 123 (FIG. 2) or the Triangle of Koch 125 (FIG. 2). The left ventricle pacing conductor pair 324 leads to the left ventricle electrode 420, which may be positioned at locations such as within a lateral branch of the coronary sinus vein spanning the left ventricle 112.

The heart 100 is also connected to a lead 412 that contains the right atrium sensing conductor pair 316 and right atrium pacing conductor pair 320. The right atrium sensing conductor pair 316 and pacing conductor pair 320 lead to one or more right atrium electrodes 406. The right atrium electrode 406 may be positioned at various locations such as the sino-atrial node 120 or at the appendage area 119 of the right atrium 106. As previously discussed, if an electrode is placed at the Triangle of Koch 125 (FIG. 2), then the right atrium and left atrium pacing may be done through a single pacing conductor pair that leads to the electrode at the Triangle of Koch 125.

An additional lead 422 is connected to the heart 100, and the lead 422 contains the right ventricle sensing conductor pair 318 and pacing conductor pair 326. The right ventricle sensing conductor pair 318 and pacing conductor pair 326 lead to one or more right ventricle electrodes 418. The right ventricle electrode 418 may be positioned at various locations such as the apex or septum wall of the right ventricle 108.

Figure 5:
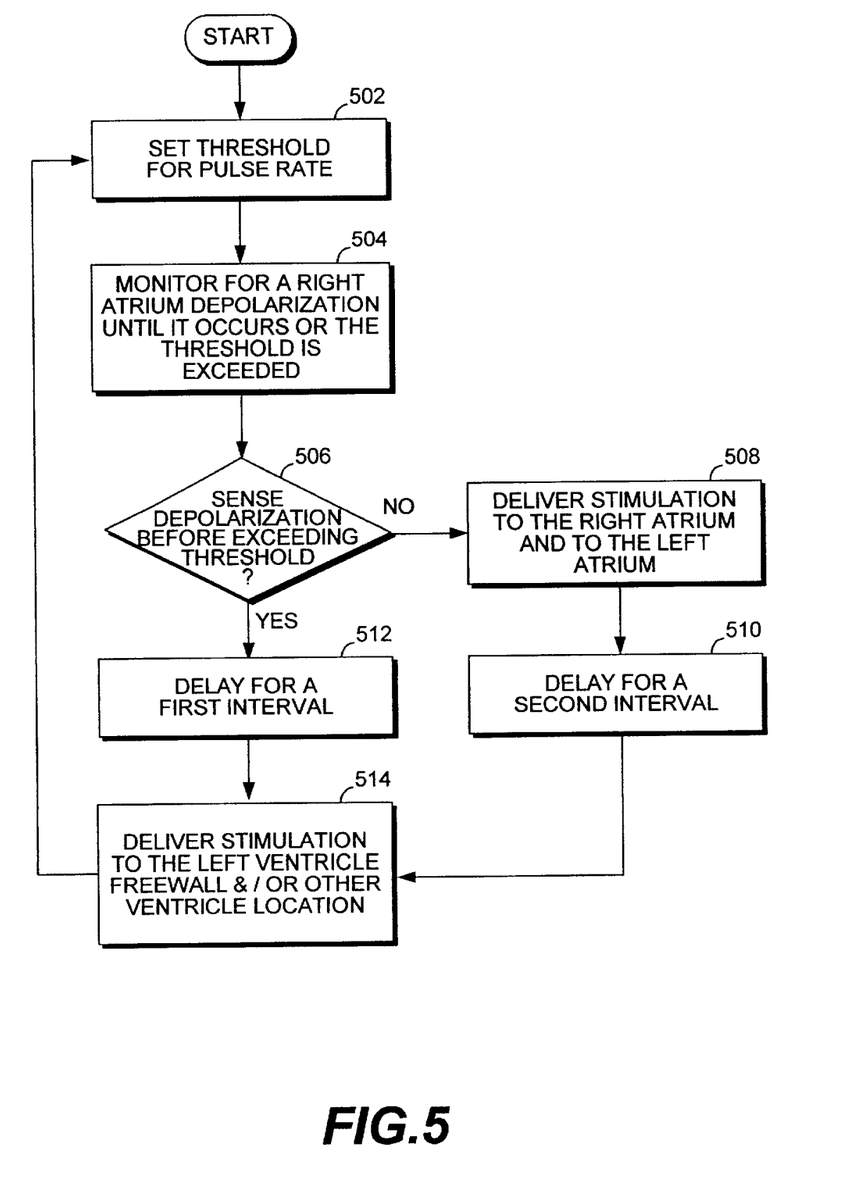
FIG. 5 is a flowchart depicting an exemplary method for providing cardiac resynchronization therapy by sensing a depolarization at the sino-atrial node in the right atrium when allowing a natural pulse rate and by providing a pacing signal in proximity to the left atrium when controlling the pulse rate.

FIG. 5 is a flowchart depicting an exemplary method of the present invention, such as executed by the CRT device 300, when providing CRT to the heart 100. This embodiment of the operations of the invention may be implemented as logical operations in the system. The logical operations are implemented (1) as a sequence of computer implemented steps running on a computer system of the implantable or external CRT device 300, and/or (2) as interconnected machine modules running within the computing system of the CRT device 300.

This implementation is a matter of choice dependent on the performance requirements of the CRT device 300 implementing the invention. Accordingly, the logical operations making up the embodiments of the invention described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The exemplary method shown in FIG. 5 begins at threshold operation 502 where a threshold of time may be determined. This threshold of time corresponds to an amount of time within which a natural depolarization stemming from the sino-atrial node 120 should occur after ventricular activity. This threshold is therefore used as the deciding factor in whether the natural pulse rate is adequate. This threshold may be set at a fixed baseline value used in every cardiac cycle when rate responsiveness operation is not desired. Alternatively, the threshold may be dynamically set at threshold operation 502 for each cardiac cycle based on the patient's physical state when rate responsiveness is desired. The manner of setting the threshold at a fixed baseline value or dynamically setting the threshold based on the patient's physical state is known to those skilled in the art.

After setting the threshold, flow moves to monitor operation 504 where the sensing module 304 is instructed to monitor for a depolarization at the right atrium electrode 406. The monitor operation 504 continues for a length of time equal to the threshold or until a depolarization is sensed at the right atrium electrode 406. By placing the electrode 406 used for atrial sensing in the right atrium 106 near the sino-atrial node 120, the natural depolarization may be sensed early enough to allow timely pacing to the ventricular freewall to resynchronize ventricular contraction. Query operation 506 detects whether the sensing module 304 sensed the depolarization before the threshold expired. If not, then the cardiac cycle has not yet begun naturally and flow moves to stimulation operation 508 so that the pulse rate can be controlled by instructing the pacing module 306 to initiate the cardiac cycle. If the natural depolarization does occur prior to exceeding the threshold, then atrial pacing is inhibited by operational flow moving to delay operation 512 in preparation for providing stimulation to one or more ventricular walls.

When query operation 506 directs flow to stimulation operation 508, the pacing module 306 is instructed to provide an electrical stimulation simultaneously to the right and left atrium electrodes 406, 408 so that synchronous atrial contraction occurs. This synchronous atrial contraction permits the left atrium 110 to contract and pump blood into the left ventricle 112 well before left ventricle contraction occurs. Synchronous atrial contraction occurs because the left atrium electrode 408 generates a left atrial contraction sooner than is otherwise created by natural muscle cell propagation resulting from stimulation at the right atrium electrode 406. Because the left atrium 110 contracts early, the mitral valve does not close during left atrium contraction, and blood is not pumped back into the lungs of the patient. As discussed above, if an electrode is placed at the Triangle of Koch 125, then both the right and left atrium may be stimulated by the pacing module 306 delivering a stimulation pulse to this electrode rather than to individual electrodes in the right and left atria 106, 110.

After delivery of the stimulation pulse to the right and left atria 106, 110, flow moves to delay operation 510 where an optimized atrio-ventricular delay defining an interval (i.e., second interval) occurs. This delay is optimized to allow proper filling of the ventricles through the atrial pacing and prior to pacing of the ventricles where conduction from the atrio-ventricular node to the ventricles is not adequate. If the conduction to the septum between the ventricles is adequate, then the atrio-ventricular delay at delay operation 510 is optimized so that the stimulated freewall contraction provided by pacing module 306 after atrial stimulation is provided occurs synchronously with the natural contraction of the septum to maximize pumping efficiency. After the optimized atrio-ventricular delay has passed, flow moves to stimulate operation 514 where the one or more ventricular walls may be stimulated.

If query operation 506 has directed flow to delay operation 512, then an optimized atrio-ventricular delay defining a different interval (i.e., first interval) occurs. This delay is optimized to allow proper filling of the ventricles through natural atrial contraction prior to pacing of the ventricles where conduction from the atrio-ventricular node to the ventricles is not adequate. If the conduction to the septum between the ventricles is adequate, then the atrio-ventricular delay at delay operation 512 is optimized so that the stimulated freewall contraction provided by pacing module 306 after atrial contraction is in synchronization with the natural ventricular contraction at the septum.

Once the delay operation 510 or the delay operation 512 has completed, flow moves to stimulate operation 514 where the one or more ventricular walls are stimulated to resynchronize ventricular contraction. As discussed above, if the natural conduction through the atrio-ventricular node is satisfactory, then stimulation may be applied to the ventricular freewall of the left and/or right ventricles 112, 108 depending upon whether there is a left bundle branch and/or right bundle branch block. If natural conduction through the atrio-ventricular node is not satisfactory, then stimulation may be applied to the septum and freewalls to resynchronize the contraction. Once the ventricular stimulations have been provided, flow returns to threshold operation 502 in preparation for applying CRT during the next cardiac cycle.

Although the present invention has been described in connection with various exemplary embodiments, those of ordinary skill in the art will understand that many modifications can be made thereto within the scope of the claims that follow. Accordingly, it is not intended that the scope of the invention in any way be limited by the above description, but instead be determined by reference to the claims that follow.

What is claimed is:

1. A method for providing resynchronization therapy to a heart, comprising:
   (a) determining whether to allow the heart to proceed at a natural pulse rate;
   (b) if it is determined at step (a) that the heart should proceed at a natural pulse rate, then sensing a natural depolarization event with a first electrode in a right atrium, not stimulating the left atrium without monitoring for a depolarization within the left atrium, but subsequently stimulating one or more ventricular walls with at least a second electrode during a cardiac cycle; and
   (c) if it is determined at step (a) that the heart should not proceed at a natural pulse rate, then stimulating a left atrium with a third electrode without monitoring for a (depolarization within the left atrium and subsequently stimulating one or more ventricular walls with at least the second electrode during a cardiac cycle.

2. The method of claim 1, wherein the first electrode is positioned at a sino-atrial node.

3. The method of claim 2, wherein step (a) further comprises the step of stimulating the right atrium with the first electrode prior to stimulating the one or more ventricular walls with the second electrode during a cardiac cycle when not allowing the heart to proceed at the natural pulse rate.

4. The method of claim 3, wherein a first interval passes between sensing the natural depolarization event and stimulating the one or more ventricular walls when allowing the heart to proceed at the natural pulse rate, and wherein a second interval different than the first interval passes between stimulating the right atrium and stimulating the one or more ventricular walls when not allowing the heart to proceed at the natural pulse rate.

5. The method of claim 1, wherein the first electrode is positioned at an appendage of the right atrium.

6. The method of claim 5, wherein step (a) further comprises the step of stimulating the right atrium with the first electrode prior to stimulating the one or more ventricular walls with the second electrode during a cardiac cycle when not allowing the heart to proceed at the natural pulse rate.

7. The method of claim 1, wherein the second electrode is positioned in a coronary sinus vein adjacent the left ventricle.

8. The method of claim 1, wherein the third electrode is positioned in a coronary sinus vein adjacent the left atrium.

9. The method of claim 1, wherein the third electrode is positioned within the right atrium and atop the coronary sinus vein.

10. The method of claim 1, wherein the third electrode is positioned on the Bachman's bundle.

11. The method of claim 1, wherein the third electrode is positioned at the Triangle of Koch, the method further comprising the step of stimulating the right atrium with the third electrode while stimulating the left atrium.

12. The method of claim 1, wherein step (a) further comprises the steps of:
dynamically setting a pulse rate threshold;
during a cardiac cycle, comparing the natural pulse rate to the pulse rate threshold; and
deciding to not allow the heart to proceed at the natural pulse rate during a subsequent cardiac cycle when the comparison indicates that the natural pulse rate is below the pulse rate threshold.

13. A device for providing resynchronization therapy to a heart, comprising:
a processing module configured to determine whether to allow the heart to proceed at a natural pulse rate;
a first atrium electrode positioned to sense a depolarization in a right atrium;
one or more ventricular electrodes positioned to provide an electrical stimulation to one or more ventricular walls;
a second atrium electrode positioned to provide an electrical stimulation to a left atrium;
a sensing module in communication with the first atrium electrode, the sensing module being configured to sense a depolarization at the first atrium electrode when the processing module determines to allow the heart to proceed at the natural pulse rate; and
a pacing module configured to provide electrical stimulation to the one or more ventricular electrodes subsequent to the sensing module detecting depolarization at the first atrium electrode and not stimulate the second atrium electrode without monitoring for a depolarization within the left atrium when the processing module determines to allow the heart to proceed at the natural pulse rate, the pacing module being further configured to provide electrical stimulation to the second atrium electrode without monitoring for a depolarization within the left atrium and subsequently provide electrical stimulation to the one or more ventricular electrodes when the processing module determines to not allow the heart to proceed at the natural pulse rate.

14. The device of claim 13, wherein the first atrium electrode is positioned at a sino-atrial node.

15. The device of claim 14, wherein the pacing module is further configured to provide electrical stimulation to the first atrium electrode prior to stimulating the one or more ventricular electrodes when the processing module determines to not allow the heart to proceed at the natural pulse rate.

16. The device of claim 15, wherein a first interval passes between the sensing module sensing the depolarization and the pacing module providing electrical stimulation to the one or more ventricular electrodes when the processing module determines to allow the heart to proceed at the natural pulse rate, and wherein a second interval different than the first interval passes between the pacing module providing electrical stimulation to the first atrium electrode and providing electrical stimulation to the one or more ventricular electrodes when the processing module determines to not allow the heart to proceed at the natural pulse rate.

17. The device of claim 13, wherein the first atrium electrode is positioned at an appendage of the right atrium.

18. The device of claim 17, wherein the pacing module is further configured to provide electrical stimulation to the first atrium electrode prior to stimulating the one or more ventricular electrodes when the processing module determines to not allow the heart to proceed at the natural pulse rate.

19. The device of claim 13, wherein at least one of the one or more ventricular electrodes is positioned in a coronary sinus vein adjacent the left ventricle.

20. The device of claim 13, wherein the second atrium electrode is positioned in a coronary sinus vein adjacent the left atrium.

21. The device of claim 13, wherein the second atrium electrode is positioned within the right atrium and atop the coronary sinus vein.

22. The device of claim 13, wherein the second atrium electrode is positioned on the Bachman bundle.

23. The device of claim 13, wherein the second atrium electrode is positioned at the Triangle of Koch.

24. The device of claim 13, wherein the processing module is configured to determine whether to allow the heart to proceed at the natural pulse rate by dynamically setting a pulse rate threshold, comparing the natural pulse rate to the pulse rate threshold, and determining to not allow the heart to proceed at the natural pulse rate when the comparison indicates that the natural pulse rate is below the pulse rate threshold.

25. A device for providing resynchronization therapy to a heart, comprising:
a processing means for determining whether to allow the heart to proceed at a natural pulse rate;
a first atrium electrode means for sensing a depolarization in a right atrium;
one or more ventricular electrode means for providing an electrical stimulation to one or more ventricular walls;
a second atrium electrode means for providing an electrical stimulation to a left atrium;
a sensing means in communication with the first atrium electrode, the sensing means for sensing a depolarization at the first atrium electrode means when the processing means determines to allow the heart to proceed at the natural pulse rate; and
a pacing means for providing electrical stimulation only to the one or more ventricular electrode means subsequent to the sensing means detecting depolarization at the first atrium electrode and not stimulate the second atrium electrode means without monitoring for a depolarization in the left atrium when the processing means determines to allow the heart to proceed at the natural pulse rate, the pacing means being further configured to provide electrical stimulation to the second atrium electrode means without monitoring for a depolarization in the left atrium and subsequently provide electrical stimulation to the one or more ventricular electrode means when the processing means determines to not allow the heart to proceed at the natural pulse rate.

26. The device of claim 25, wherein the first atrium electrode means is positioned at a sino-atrial node.

27. The device of claim 26, wherein the pacing means is further configured to provide electrical stimulation to the first atrium electrode means prior to stimulating the one or more ventricular electrode means when the processing means determines to not allow the heart to proceed at the natural pulse rate.

28. The device of claim 27, wherein a first interval passes between the sensing means sensing the depolarization and the pacing means providing electrical stimulation to the one or more ventricular electrode means when the processing means determines to allow the heart to proceed at the natural pulse rate, and wherein a second interval different than the first interval passes between the pacing means providing electrical stimulation to the first atrium electrode means and providing electrical stimulation to the one or more ventricular electrode means when the processing means determines to not allow the heart to proceed at the natural pulse rate.

29. The device of claim 25, wherein the first atrium electrode means is positioned at an appendage of the right atrium.

30. The device of claim 29, wherein the pacing means is further configured to provide electrical stimulation to the first atrium electrode means prior to stimulating the one or more ventricular electrode means when the processing means determines to not allow the heart to proceed at the natural pulse rate.

31. The device of claim 25, wherein at least one of the one or more ventricular electrode means is positioned in a coronary sinus vein adjacent the left ventricle.

32. The device of claim 25, wherein the second atrium electrode means is positioned in a coronary sinus vein adjacent the left atrium.

33. The device of claim 25, wherein the second atrium electrode means is positioned within the right atrium and atop the coronary sinus vein.

34. The device of claim 25, wherein the second atrium electrode means is positioned on the Bachman bundle.

35. The device of claim 25, wherein the second atrium electrode means is positioned at the Triangle of Koch.

36. The device of claim 25, wherein the processing means is configured to determine whether to allow the heart to proceed at the natural pulse rate by dynamically setting a pulse rate threshold, comparing the natural pulse rate to the pulse rate threshold, and determining to not allow the heart to proceed at the natural pulse rate when the comparison indicates that the natural pulse rate is below the pulse rate threshold.

37. A method for providing resynchronization therapy to a heart, comprising:
   (a) determining whether to allow the heart to proceed at a natural pulse rate;
   (b) if it is determined at step (a) that the heart should proceed at a natural pulse rate, then sensing a natural depolarization event with a first electrode in a right atrium, not stimulating the left atrium, but subsequently stimulating one or more ventricular walls with at least a second electrode during a cardiac cycle; and
   (c) if it is determined at step (a) that the heart should not proceed at a natural pulse rate, then stimulating a left atrium with a third electrode, wherein the third electrode is positioned on the Bachman's bundle, and subsequently stimulating one or more ventricular walls with at least the second electrode during a cardiac cycle.

38. A method for providing resynchronization therapy to a heart, comprising:
   (a) determining whether to allow the heart to proceed at a natural pulse rate;
   (b) if it is determined at step (a) that the heart should proceed at a natural pulse rate, then sensing a natural depolarization event with a first electrode in a right atrium, not stimulating the left atrium, but subsequently stimulating one or more ventricular walls with at least a second electrode during a cardiac cycle; and
   (c) if it is determined at step (a) that the heart should not proceed at a natural pulse rate, then stimulating a left atrium with a third electrode, wherein the third electrode is positioned at the Triangle of Koch, the method further comprising the step of stimulating the right atrium with the third electrode while stimulating the left atrium, and subsequently stimulating one or more ventricular walls with at least the second electrode during a cardiac cycle.

39. A method for providing resynchronization therapy to a heart, comprising:
   (a) determining whether to allow the heart to proceed at a natural pulse rate, wherein the determination comprises dynamically setting a pulse rate threshold, during a cardiac cycle comparing the natural pulse rate to the pulse rate threshold, and deciding to not allow the heart to proceed at the natural pulse rate during a subsequent cardiac cycle when the comparison indicates that the natural pulse rate is below the pulse rate threshold;
   (b) if it is determined at step (a) that the heart should proceed at a natural pulse rate, then sensing a natural depolarization event with a first electrode in a right atrium, not stimulating the left atrium, but subsequently stimulating one or more ventricular walls with at least a second electrode during a cardiac cycle; and
   (c) if it is determined at step (a) that the heart should not proceed at a natural pulse rate, then stimulating a left atrium with a third electrode, and subsequently stimulating one or more ventricular walls with at least the second electrode during a cardiac cycle.

* * * * *

UNITED STATES PATENT AND TRADEMARK OFFICE
CERTIFICATE OF CORRECTION

PATENT NO. : 6,701,186 B2  Page 1 of 1
DATED : March 2, 2004
INVENTOR(S) : Spinelli et al.

It is certified that error appears in the above-identified patent and that said Letters Patent is hereby corrected as shown below:

<u>Column 10,</u>
Line 27, "(depolarization" should read -- depolarization --

Signed and Sealed this

Eighth Day of June, 2004

JON W. DUDAS
*Acting Director of the United States Patent and Trademark Office*